United States Patent
Proctor et al.

(10) Patent No.: US 10,667,830 B2
(45) Date of Patent: Jun. 2, 2020

(54) COLLAGEN STIMULATION DEVICE AND METHODS

(71) Applicant: Bellus Medical, LLC, Dallas, TX (US)

(72) Inventors: Joseph Proctor, Dallas, TX (US); Tanzeel Ur Rahman, Strongsville, OH (US); Ronald J Hegler, North Royalton, OH (US); David J Lapeus, Medina, OH (US); James Mullner, Hudson, OH (US)

(73) Assignee: BELLUS MEDICAL, LLC, Dallas, TX (US)

( * ) Notice: Subject to any disclaimer, the term of this patent is extended or adjusted under 35 U.S.C. 154(b) by 221 days.

(21) Appl. No.: 15/566,665

(22) PCT Filed: Apr. 13, 2016

(86) PCT No.: PCT/US2016/027382
§ 371 (c)(1),
(2) Date: Oct. 13, 2017

(87) PCT Pub. No.: WO2016/168374
PCT Pub. Date: Oct. 20, 2016

(65) Prior Publication Data
US 2018/0103968 A1  Apr. 19, 2018

Related U.S. Application Data

(60) Provisional application No. 62/146,939, filed on Apr. 13, 2015.

(51) Int. Cl.
*A61B 17/20* (2006.01)
*A61M 5/32* (2006.01)
(Continued)

(52) U.S. Cl.
CPC ......... *A61B 17/205* (2013.01); *A61M 5/3287* (2013.01); *A61M 5/46* (2013.01);
(Continued)

(58) Field of Classification Search
CPC ... A61B 17/205; A61B 17/34; A61B 17/3403; A61B 17/3478; A61B 17/3494;
(Continued)

(56) References Cited

U.S. PATENT DOCUMENTS 7,901,387 B2 * 3/2011 Stemme ............ A61M 37/0015
604/173
8,135,475 B2   3/2012 Kreindel et al.
(Continued)

FOREIGN PATENT DOCUMENTS

CH    396311 A    7/1965
CN   2030490 U    1/1989
(Continued)

OTHER PUBLICATIONS

Agarwal et al., "Chemical reconstruction of skin scars therapy using 100% trichloroacetic Acid in the treatment of atrophic facial post varicella scars: a pilot study," J Cutan Aesthet Surg. Jul. 2013;6(3):144-7.
(Continued)

*Primary Examiner* — Ryan J. Severson
(74) *Attorney, Agent, or Firm* — Michael Best & Friedrich LLP (57) ABSTRACT

Device for safely and precisely causing micro-injuries to the dermis to stimulate collagen production a skim remodeling. Specifically, needles on the device pierce the epidermis and basal cell layer into the dermis. The device incorporates safety features for the operator to be able to operate the device with one hand while keeping the other had free during procedures. Additionally, the device incorporates single use safety controls to help prevent cross contamination between patients.

15 Claims, 3 Drawing Sheets

(51) Int. Cl.
  *A61M 5/46* (2006.01)
  *A61M 37/00* (2006.01)
  *A61B 17/00* (2006.01)
  *A61B 90/00* (2016.01)
  *A61B 90/98* (2016.01)
  *A61B 17/54* (2006.01)
  *A61B 50/36* (2016.01)

(52) U.S. Cl.
  CPC ......... *A61M 37/0015* (2013.01); *A61B 17/54* (2013.01); *A61B 50/362* (2016.02); *A61B 90/98* (2016.02); *A61B 2017/00747* (2013.01); *A61B 2017/00765* (2013.01); *A61B 2017/00792* (2013.01); *A61B 2090/034* (2016.02); *A61B 2090/0803* (2016.02); *A61B 2090/0814* (2016.02); *A61M 5/3298* (2013.01)

(58) Field of Classification Search
  CPC .. A61B 2017/00747; A61B 2017/3405; A61B 2017/3409; A61B 2090/0814; A61M 5/3295; A61M 5/3298; A61M 5/50
  See application file for complete search history.

(56) References Cited

U.S. PATENT DOCUMENTS

| | | | |
|---|---|---|---|
| 8,900,181 B2 | 12/2014 | Knowlton | |
| 8,915,937 B2 | 12/2014 | Nagao et al. | |
| 8,920,379 B2* | 12/2014 | Lee | A61M 37/0076 604/173 |
| 8,951,216 B2* | 2/2015 | Yoo | A61H 7/005 601/101 |
| 9,039,688 B2* | 5/2015 | Palmer, III | A61B 18/02 606/20 |
| 9,061,128 B2 | 6/2015 | Hall et al. | |
| 9,066,738 B2* | 6/2015 | Mehta | A61B 18/14 |
| 9,168,198 B2* | 10/2015 | Lee | A61H 23/006 |
| 9,227,021 B2* | 1/2016 | Buss | A61M 5/3134 |
| 9,320,536 B2* | 4/2016 | Na | A61N 1/30 |
| 9,358,376 B2* | 6/2016 | Altarac | A61M 37/0015 |
| 9,439,673 B2* | 9/2016 | Austen | A61B 17/205 |
| 9,504,813 B2* | 11/2016 | Buss | A61M 5/3134 |
| 9,596,920 B2* | 3/2017 | Shalev | A45D 44/22 |
| 9,629,991 B1* | 4/2017 | O'Brien, III | A61N 1/40 |
| 9,636,491 B1* | 5/2017 | O'Brien, III | A61M 37/0015 |
| 9,717,863 B2* | 8/2017 | Davies | A61M 5/34 |
| 9,775,774 B2* | 10/2017 | Na | A61H 15/02 |
| 9,987,475 B2* | 6/2018 | Kim | A61H 15/0092 |
| 10,086,035 B2* | 10/2018 | Garruto | A61K 8/26 |
| 10,220,195 B2* | 3/2019 | O'Brien, III | A61M 5/2033 |
| 10,286,030 B2* | 5/2019 | Garruto | A61K 8/26 |
| 10,327,800 B2* | 6/2019 | Austen | A61B 17/205 |
| 10,369,341 B2* | 8/2019 | Lee | A61H 39/08 |
| 2005/0113750 A1 | 5/2005 | Targell | |
| 2005/0203575 A1* | 9/2005 | Carson | A61M 37/0015 606/204.35 |
| 2008/0033356 A1* | 2/2008 | Kluge | A61B 5/0531 604/117 |
| 2008/0039806 A1* | 2/2008 | Stemme | A61M 37/0015 604/272 |
| 2009/0137945 A1 | 5/2009 | Marquez | |
| 2009/0157094 A1 | 6/2009 | Yeshurun et al. | |
| 2009/0312691 A1* | 12/2009 | Kim | A61H 15/0092 604/22 |
| 2010/0010486 A1* | 1/2010 | Mehta | A61B 18/14 606/41 |
| 2010/0023003 A1* | 1/2010 | Mulholland | A61B 17/205 606/33 |
| 2010/0249772 A1 | 9/2010 | Mehta et al. | |
| 2011/0118638 A1* | 5/2011 | Yoo | A61H 7/005 601/108 |
| 2011/0319865 A1* | 12/2011 | Buss | A61M 5/3134 604/506 |
| 2012/0041374 A1* | 2/2012 | Lee | A61M 37/0076 604/173 |
| 2012/0150266 A1* | 6/2012 | Shalev | A45D 44/22 607/99 |
| 2012/0265187 A1* | 10/2012 | Palmer, III | A61B 18/02 606/21 |
| 2013/0102956 A1 | 4/2013 | Hertzog | |
| 2013/0345616 A1 | 12/2013 | Chang | |
| 2014/0039523 A1* | 2/2014 | Austen | A61B 17/205 606/131 |
| 2014/0114220 A1* | 4/2014 | Lee | A61H 23/006 601/107 |
| 2014/0128685 A1* | 5/2014 | Na | A61N 1/30 600/249 |
| 2014/0303555 A1* | 10/2014 | Davies | A61M 5/34 604/110 |
| 2015/0231382 A1* | 8/2015 | Altarac | A61M 37/0015 604/47 |
| 2016/0089527 A1* | 3/2016 | Buss | A61M 5/3134 604/506 |
| 2016/0192961 A1* | 7/2016 | Ginggen | A61B 18/02 604/173 |
| 2016/0361229 A1* | 12/2016 | Na | A61H 15/02 |
| 2016/0367280 A1* | 12/2016 | Austen | A61B 17/205 |
| 2017/0120024 A1* | 5/2017 | Lee | A61M 5/158 |
| 2017/0143958 A1* | 5/2017 | Shalev | A45D 44/22 |
| 2017/0224760 A1* | 8/2017 | Garruto | A61K 8/26 |
| 2017/0354810 A1* | 12/2017 | O'Brien, III | A61M 5/2033 |
| 2018/0103968 A1* | 4/2018 | Proctor | A61B 17/205 |
| 2018/0104145 A1* | 4/2018 | Na | A61H 15/02 |
| 2018/0289767 A1* | 10/2018 | Garruto | A61K 8/26 |
| 2019/0151674 A1* | 5/2019 | Yoon | A61B 18/203 |
| 2019/0160274 A1* | 5/2019 | O'Brien, III | A61M 5/2033 |

FOREIGN PATENT DOCUMENTS

| | | |
|---|---|---|
| CN | 1819852 A | 8/2006 |
| CN | 2834422 Y | 11/2006 |
| CN | 102395394 A | 3/2012 |
| CN | 202173684 U | 3/2012 |
| CN | 202236856 U | 5/2012 |
| CN | 202620474 U | 12/2012 |
| CN | 202740626 U | 2/2013 |
| EP | 2377475 A1 | 10/2011 |
| JP | 2014018431 A | 2/2014 |
| KR | 20100034836 A | 2/2010 |
| WO | WO 2011/039728 A1 | 4/2011 |

OTHER PUBLICATIONS

Arora et al., "Dependence of collagen remodelling on alpha-smooth muscle actin expression by fibroblasts," J Cell Physiol, 1994, 159(1):161-75.
Cicchi et al., "In vivo non-invasive monitoring of collagen remodelling by two-photon microscopy after micro-ablative fractional laser resurfacing," J Biophotonics. Nov. 2014;7(11-12):914-25.
Karsai et al., "Pulsed dye laser: what's new in nonvascular lesions?" J Eur Acad Dermatol Venereal. Aug. 2007;21(7):877-90.
Michel, "ED2000: 585 nm collagen remodelling pulsed dye laser," J Cosmet Laser Ther, 2003, 5(3-4):201-3.
Trelles et al., "Non-ablative facial skin photorejuvenation with an intense pulsed light system and adjunctive epidermal care," Lasers Med Sci, 2003, 18(2):104-11.
International Search Report and Written Opinion for Application No. PCT/US2016/027382 dated Jul. 15, 2016 (7 pages).
Chinese Patent Office Action for Application No. 201680021912.4 dated Jun. 19, 2019 (19 pages, English translation included).
European Patent Office Action for Application No. 16780685.0 dated Jul. 19, 2019 (8 pages).
Chinese Patent Office Action for Application No. 201680021912.4 dated Jan. 20, 2020 (14 pages, English translation included).

* cited by examiner

COLLAGEN STIMULATION DEVICE AND METHODS

CROSS REFERENCE TO RELATED APPLICATIONS

This application claims priority to U.S. provisional application No. 62/146,939 filed Apr. 13, 2015, which claims priority to PCT application number PCT/US16/27382, and hereby incorporates the contents thereof.

TECHNICAL FIELD

This invention relates to the delivery of a needle through the epidermis and into the dermis. Collagen growth is stimulated by injury to the skin. Uncontrolled injury of the dermis can trigger collagen over stimulation and create scar tissue and keloids. Controlled micro-injury to the dermis causes collagen to be produced in a relatively controlled manner to restore elasticity to older skin. Additionally, in the cases of scar tissue and keloids micro-injury can cause remodeling of the tissue to reduce the overall appearance of the scar.

BACKGROUND

The global demand for medical aesthetic devices has been estimated to be 4.8 billion dollars. The growth for medical aesthetic devices is expected to grow 12.2% year over year through at least 2018.

Numerous examples of medical aesthetic devices exist in the prior art.

Non-Patent Citations

J Biophotonics. 2014 November; 7(11-12):914-25. doi: 10.1002/jbio.201300124. Epub 2013 Dec. 11. Title: In vivo non-invasive monitoring of collagen remodelling by two-photon microscopy after micro-ablative fractional laser resurfacing. Authors: Cicchi R1, Kapsokalyvas D, Troiano M, Campolmi P, Morini C, Massi D, Cannarozzo G, Lotti T, Pavone F S.

Abstract: Non-linear optical microscopy is becoming popular as a non-invasive in vivo imaging modality in dermatology. In this study, combined TPF and SHG microscopy were used to monitor collagen remodelling in vivo after micro-ablative fractional laser resurfacing. Papillary dermis of living subjects, covering a wide age range, was imaged immediately before and forty days after treatment. A qualitative visual examination of acquired images demonstrated an age-dependent remodelling effect on collagen. Additional quantitative analysis of new collagen production was performed by means of two image analysis methods. A higher increase in SHG to TPF ratio, corresponding to a stronger treatment effectiveness, was found in older subjects, whereas the effect was found to be negligible in young, and minimal in middle age subjects. Analysis of collagen images also showed a dependence of the treatment effectiveness with age but with controversial results. While the diagnostic potential of in vivo multiphoton microscopy has already been demonstrated for skin cancer and other skin diseases, here we first successfully explore its potential use for a non-invasive follow-up of a laser-based treatment.

J Cutan Aesthet Surg. 2013 July; 6(3):144-7. doi: 10.4103/0974-2077.118408. Title: Chemical reconstruction of skin scars therapy using 100% trichloroacetic Acid in the treatment of atrophic facial post varicella scars: a pilot study. Authors: Agarwal N1, Mittal A, Kuldeep C, Gupta L K, Khare A K, Mehta S.

Abstract: Chickenpox (varicella) is a common viral disease caused by Varicella zoster virus. Facial atrophic scars after varicella infection are not uncommon and pose a cosmetic problem. Like atrophic scars of other aetiologies, they are a difficult condition to treat. There are not enough references in the literature regarding efficient treatment of post varicella scars. High strength Trichloroacetic acid (TCA), which is known to cause dermal collagen remodelling, was used to treat varicella scars in the present study. The study was undertaken to assess the efficiency of Chemical Reconstruction of Skin Scars (CROSS) technique using 100% TCA in the treatment of atrophic facial post varicella scars.

MATERIALS AND METHODS: A total of 16 patients with atrophic facial post varicella scars were treated by focal application of 100% TCA solution by pressing down upon the scar surface by a toothpick (CROSS technique). Total 4 sittings were given at 2 weekly intervals and the results evaluated after 3 months of follow-up. Statistical analysis was carried out using Fischer's exact t-test.

RESULTS: All of the 13 patients who completed the study showed good clinical improvement, with 69% patients grading the response as excellent (>75%) improvement, whereas the rest 31% patients reporting good (51-75%) improvement. No significant complications were seen in any patient.

CONCLUSIONS: CROSS technique using 100% TCA is a safe, cheap and effective therapy for the treatment of post varicella scars.

J Eur Acad Dermatol Venereol. 2007 August; 21(7):877-90. Title: Pulsed dye laser: what's new in non-vascular lesions? Authors: Karsai S1, Roos S, Hammes S, Raulin C.

Abstract: In dermatology, the pulsed dye laser (PDL) is the therapeutic instrument of choice for treating most superficial cutaneous vascular lesions. In addition, clinical experience over the last decade allowed us to treat patients with an ever increasing number of non-vascular indications. The purpose of this report is to summarize and critically appraise the scientific evidence that support the role of PDL in treating non-vascular skin lesions.

METHODS: A literature-based study has been conducted, including the review of publications over the period January 1995 to December 2006, using the Medline Database. We also included our own experience in managing non-vascular lesions with the PDL. Four sets of preoperative and postoperative photos are presented.

RESULTS: For viral skin lesions, PDL proved to be an alternative to other therapy options. This applies particularly to periungual warts and mollusca contagiosa. The mechanism of PDL with inflammatory dermatoses has not yet been elucidated. The effect seems to be better if there is a vascular component to the disease. With most of these indications (such as psoriasis and acne), PDL currently plays a rather minor or complementary role. Regarding collagen remodelling (hypertrophic scars, keloids, stretch marks, and skin rejuvenation), the question of whether a therapy makes sense or not has to be decided from case to case.

CONCLUSION: With PDL, it is possible to achieve good results with numerous, partly less well-known indications (i.e. lupus erythematosus). With other diseases, PDL has so far been considered to be a complementary therapy method or to be in an experimental state.

J Cosmet Laser Ther. 2003 December; 5(3-4):201-3. Title: ED2000: 585 nm collagen remodelling pulsed dye laser. Author: Michel JL1.

Abstract: The wavelength of 585 nm corresponds to an absorption peak of haemoglobin. The heating effect in these skin layers triggers the release of various growth factors that stimulate collagen remodelling and tightening. We report our experience with a 585 nm collagen remodelling, double flashlamp excited pumped dye laser was used (ED2000, Deka MELA, Calenzano, Italy), spot size 5 mm, energy density (fluence J/cm(2)) from 2 to 4 J/cm(2), emission modality (repetition rate) at 0.5 Hz, with a short pulse duration of 250 microsec. The efficiency of 585 nm collagen remodelling pulsed dye laser is controversial in only one session. It is probably reasonable to inform patients that 3-4 treatment sessions are necessary, and that 10% of the patients have no response to nonablative photorejuvenation. Because of its low fluence and its shorter pulse duration, the 585 nm collagen remodelling pulsed dye laser has limited efficacy for the treatment of port wine stains. However, it may offer patients with erythematous, raised or hypertrophic acne scars or striae distensae a permanent cosmetic solution. This laser is safe and effective in the treatment of surgical scars starting as soon as possible, on the day of suture removal if possible. We found that 96.3% of molluscum contagiosum healed after the first treatment, the other 3.7% after the second.

Lasers Med Sci. 2003; 18(2):104-11. Title: Non-ablative facial skin photorejuvenation with an intense pulsed light system and adjunctive epidermal care. Authors: Trelles MA1, Allones I, Velez M.

Abstract: Laser skin resurfacing is popular, but the appearance of the face during healing is unpleasant. Non-ablative photorejuvenation with intense pulsed light (IPL) has been reported as being successful but with varied results. In this study we sought the possibility of enhancing the clinical effects with adjunctive epidermal care. Twenty-five women aged from 32 to 68, skin types I-IV, with a variety of wrinkle types and other conditions associated with photoaged skin, were treated with IPL according to our parameters over six sessions coupled with an adjunctive pretreatment micropeel and applications of nutritive and antipigmenting creams. Macroscopic and histological assessments were performed. At weeks 4 and 8 fair to good satisfaction was noted in 17 and 19 patients, and poor satisfaction in 8 and 6 patients, respectively. The histology showed good dermal collagen remodelling in all cases, with a reduction in elastosis. The results of IPL photorejuvenation can be enhanced, as our trials showed. The good patient satisfaction obtained was clearly demonstrated in the histologies and evaluations throughout the study.

J Cell Physiol. 1994 April; 159(1):161-75. Title: Dependence of collagen remodelling on alpha-smooth muscle actin expression by fibroblasts. Author: Arora PD1, McCulloch C A.

Abstract: To study the relation between expression of the putative myofibroblast marker alpha-smooth muscle actin and the remodelling of extracellular matrix, immunocytochemical, gel electrophoresis, and collagen gel contraction studies were performed on two human fibroblast subtypes. Double immunolabelling for total actins and alpha-smooth muscle (sm) actin as well as affinity labelling of filamentous and monomeric actins in gingival fibroblasts demonstrated that alpha-sm was colocalized in stress fibres and in regions with high levels of monomeric actin throughout the cytoplasm. alpha-sm comprised up to 14% of total cellular actin as assessed by 2D gel electrophoresis. Thirteen different gingival and seven different periodontal ligament fibroblast lines constitutively expressed on alpha-sm actin. These cells exhibited up to 60% inter-line variations of fluorescence due to alpha-sm actin and up to 70% and 45% inter-line variation in the rate of collagen gel contraction. Quantitative, single cell fluorimetry of alpha-sm actin immunoreactivity demonstrated a linear relation between gel contraction and alpha-sm actin (correlation coefficients of 0.71 for gingival and 0.61 for periodontal ligament cells), but there was no detectable relationship between total actin content and gel contraction. In contrast, flow cytometry demonstrated that 99% of the total gated cells from cell lines exhibiting rapid gel contraction showed alpha-sm actin staining above background fluorescence as compared to only 35% of cells with slow rates of gel contraction. Contracting collagen gels stained with FITC-phalloidin showed cells with well-developed stress fibres that were progressively more compact and elongated during the time of maximal gel contraction. To examine the dependence of gel contraction on assembly of monomeric actin into actin filaments, cells were electroporated in the presence of phalloidin or cytochalasin D. Collagen gels exhibited up to 100% inhibition of gel contraction that was dose-dependent. Gel contraction was inhibited 93% by electroinjection of cells with alpha-sm actin antibody prior to incubation, but the antibody did not inhibit actin assembly after attachment and spreading on substrates. These data indicate that gel contraction is dependent on alpha-sm actin expression and that alpha-sm actin is a functional marker for a fibroblast subtype that rapidly remodels the extracellular matrix.

Patent Application Citations

U.S. patent application Ser. No. 12/307,315 from Kim et al., discloses "a micro needle roller assembly comprising a roller head including an external cylindrical member having a plurality of micro needles mounted on a surface thereof and an internal member placed in the external member and supported to the external member by supporting piece; and a handling member coupled to the internal member for rotating the internal member of the roller head; the micro needles, the external cylindrical member and the internal member being made of polymer resin."

U.S. patent application Ser. No. 12/972,013 to Knowlton discloses a "new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site."

U.S. patent application Ser. No. 13/715,134 to Hertzog discloses a "hollow needle for attachment to a syringe, through which a liquid can be delivered to the stratum granulosum and/or beneath the epidermis, preferably to an area consisting from the stratum granulosum (included) to reticular dermis (included) and more preferably beneath the papillary dermis during a cosmetic procedure, the needle comprising a distal tip and including a lateral aperture adjacent to the distal tip, wherein the liquid exits the needle via the lateral aperture, and wherein the needle is flexible.

Apparatus comprising a needle of the invention and a syringe, and a method of use thereof, is also provided."

U.S. patent application Ser. No. 13/683,995 to Chang discloses a "device and methods for increasing the permeability of the skin's surface to fluid and/or drug delivery is described. The device comprises an abrasive media to remove the outer layer of the stratum corneum, while at the same time applying an electric current that stimulates the skin under the stratum corneum, and delivers fluids from a supply reservoir. The device may also have a vacuum function which evacuates fluid and skin debris from the surface of the skin and delivers the evacuated fluid and skin debris to a waste (or collection) container."

U.S. patent application Ser. No. 13/825,083 to Na discloses "methods and systems for dermatologic treatments" including precise delivery of needles to the skin.

U.S. patent application Ser. No. 14/214,188 to Hall et al., discloses a "system for delivering light and/or ultrasound across a skin surface is provided. The system includes a device having a layered structure comprising one or both of a light source and an ultrasonic transducer. The light source comprises a flexible light emitter layer electrically coupled to a first conductive layer and a second conductive layer, wherein at least one of the first and second conductive layers is transparent. The ultrasonic transducer comprises a flexible ultrasound emitter layer electrically coupled to a third conductive layer and a fourth conductive layer. The system also includes one or more sensors in contact with the skin surface and a controller electrically coupled to the device and the sensor. The controller is operable to receive sensor data from the sensor and dynamically control the device in response to the received sensor data."

U.S. patent application Ser. No. 13/938,625 to Nagao et al., discloses a "puncture needle cartridge which can prevent a used lancet from being reused. A puncture needle cartridge includes a puncture needle holder configured to be cylindrical, placed on an outer circumferential surface of a lancet body, and provided with an opening through which a puncture needle is allowed to protrude, and a protective cap adapted to cover and protect the opening and configured to be separable from the puncture needle holder. The protective cap includes a base adapted to cover the opening when the protective cap is joined and a pair of raised walls which protrude from the base toward the puncture needle holder and whose tip portions are placed facing each other. Tip portions of the raised walls pinch the puncture needle holder by spreading against elastic deformation when the protective cap is joined to the puncture needle holder, and when the protective cap is separated from the puncture needle holder, a space between the tip portions becomes smaller than outside diameter of the puncture needle holder due to elastic deformation."

U.S. patent application Ser. No. 12/222,063 to Kreindel et al., discloses an "applicator for skin treatment having one or more RF electrodes. An article is located between the electrodes, such as a roller or flexible belt containing one or more protruding pins electrically isolated from the RF electrodes. The invention also provides a system for skin treatment comprising the applicator of the invention and a control unit. The invention further provides a method of treating skin disorders in which a section of the skin is heated while, essentially simultaneously, piercing one or more holes in the heated section of the skin. The method of the invention may be used, for example, in collagen remodeling." U.S. patent application Ser. No. 12/412,201 to Mehta et al., discloses "a system and method for percutaneous energy delivery in an effective, manner using one or more probes to effect a cosmetic improvement in tissue."

U.S. patent application Ser. No. 12/277,845 to Marquez discloses a "device for creating a plurality of small wounds in a patient's skin and introducing topically-applied substances therein is disclosed. The device comprises a rigid plate that has a top side, a bottom side, and at least one peripheral edge that connects the top and bottom sides. The device further includes a tool attachment means fixed with the top side of the plate and adapted to fix the device to a motorized tool that oscillates reciprocally back and forth along the longitudinal axis of the plate. A plurality of needles project generally orthogonally away from the bottom side of the plate. In use, the plate is fixed with the tool and the tool activated. The bottom side of the plate is then applied to the skin of the patient such that each needle repeatedly pierces same to create the plurality of small wounds therein. When the substance is applied to the skin first, each needle draws a portion of the substance into the skin with each oscillation of the tool."

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The invention may seek to satisfy one or more of the above-mentioned desires. Although the present invention may obviate one or more of the above-mentioned desires, it should be understood that some aspects of the invention might not necessarily obviate them.

SUMMARY OF THE INVENTION

The exemplary embodiment of the present invention addresses safety issues with respect to an operator being able to load and unload needles safely with one hand while maintaining the other hand free during the procedure. Accordingly, an aspect of the present invention is to provide a separable module for housing needles. The present invention provides an apparatus and system to reduce cross-contamination between patients. Accordingly, an aspect of the present invention is to provide a control and reporting means so that a needle module may only be used one time or controlled by external means such as a preset time, RFID communication, or physical impairment. The present invention provides a needle to reduce the overall amount of damage to the dermis than by commonly used round needle tips. Accordingly, an aspect of the invention is to provide an X-shaped needle to reduce the cross-section of the needle point over a certain depth of penetration into the dermis. The present invention provides for a sensing system to determine the needle point position relative to the epidermis to dermis junction. Accordingly, an aspect of the invention is to provide a sensing mechanism and a microprocessor to modulate the depth, frequency, and power of needle movement during operation.

DETAILED DESCRIPTION

Figure 1:
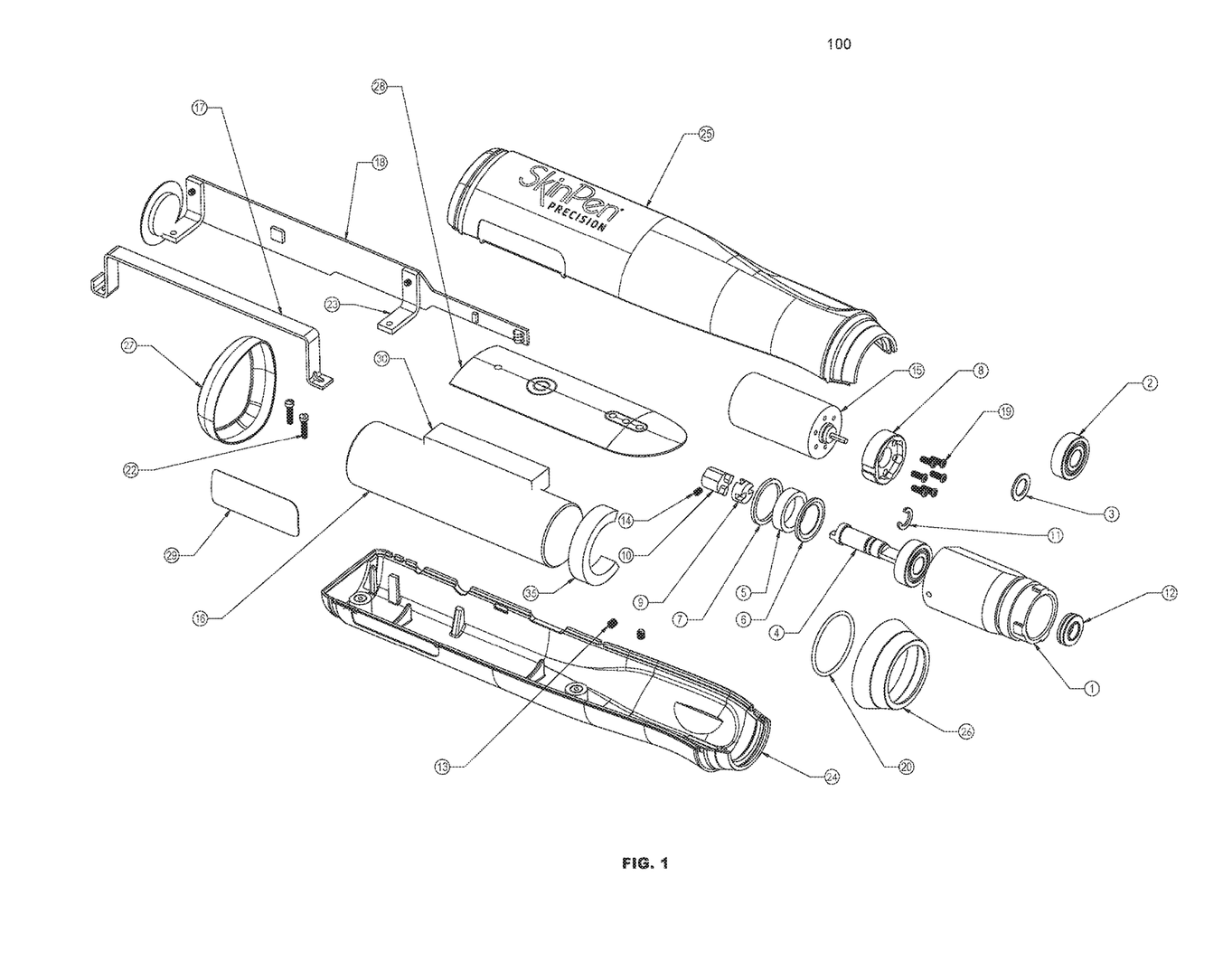
FIG. 1 shows an exploded view of a preferred embodiment of a single handed operable needle module upper end.

Referring to FIG. 1 an exploded view of the upper end of the pen system is comprised of the following parts:

| ITEM NO. | DESCRIPTION |
| --- | --- |
| 1 | Pen Tip |
| 2 | Bearing 5 × 13 × 4 |
| 3 | Bearing Spacer |
| 4 | Pen Shaft |
| 5 | Wave Spring |
| 6 | Wave Spring Adapter |
| 7 | Spiral Snap Ring |
| 8 | Motor Mounting Cup |
| 9 | Spider Coupling |
| 10 | Motor Shaft Coupling |
| 11 | Snap Ring |
| 12 | Rotary Seal |
| 13 | M2x0.4 × 2.5 LG SET SCREW |
| 14 | M1.6x0.35 × 2.5 LG SET SCREW |
| 15 | DC Motor |
| 16 | Battery, Rechargeable Li, 3.7 V, 2.6 Ah |
| 17 | Battery Bracket |
| 18 | PCB Assem |
| 19 | M1.6X0.35 PH SCREW |
| 20 | Oring |
| 22 | 0-80 screw |
| 23 | PCBA Bracket |
| 24 | Case Handle, Left |
| 25 | Case Handle, Right |
| 26 | Cowl, Front |
| 27 | Cowl, Rear |
| 28 | Case Handle Overlay |
| 29 | Label |
| 30 | Battery Compression Strip |
| 31 | Threadlocker |
| 32 | Epoxy |
| 33 | Flat Black Paint |
| 34 | Thermal Gel |
| 35 | Housing Stabilizer |
| 36 | Sensor Eye Hold down |
| 37 | Electrical Insulation Tape |

Figure 2A:
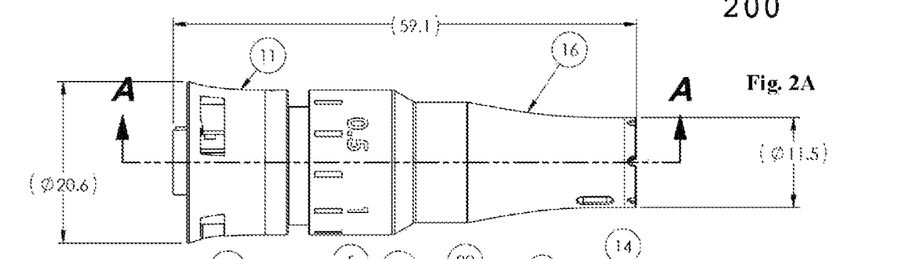
FIG. 2A shows a preferred embodiment of a single handed operable needle module connection system with a lower end disposable needle 200.
Figure 2B:
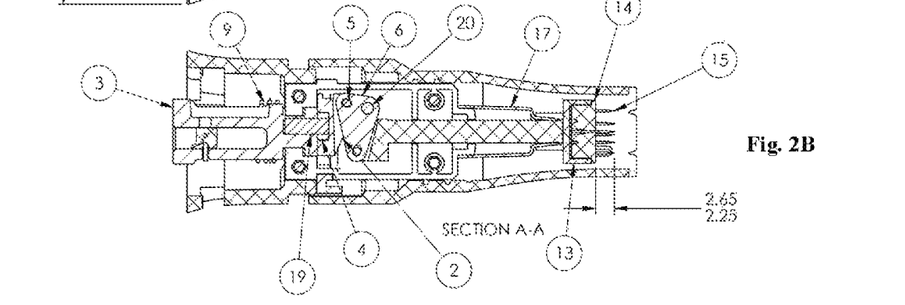
FIG. 2B shows a cut away of the preferred embodiment of a single handed operable needle module connection system with a lower end disposable needle 200.
Figure 3A:
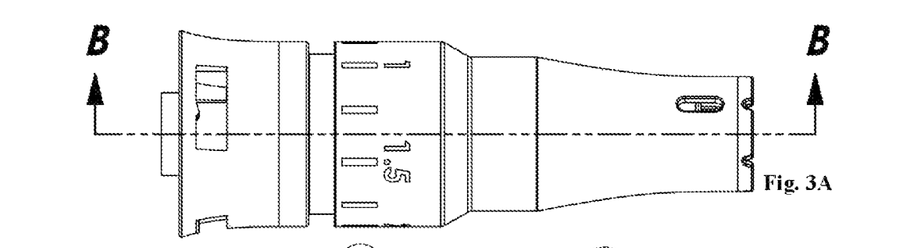
FIG. 3A shows a preferred embodiment of a single handed operable needle module connection system with an upper and lower end connected.
Figure 3B:
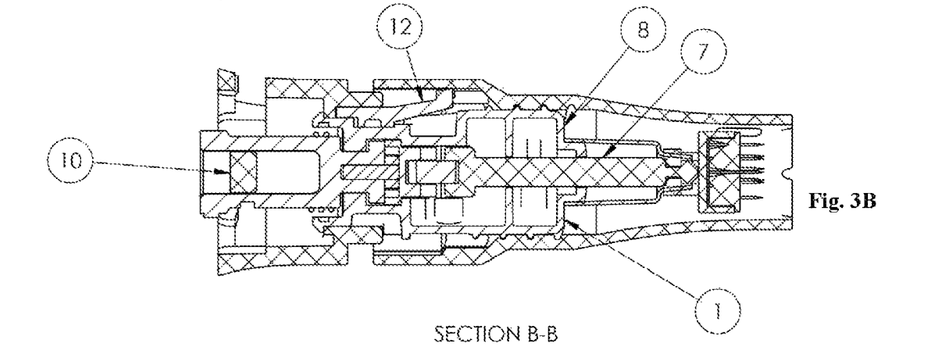
FIG. 3B shows a cut away of the preferred embodiment of a single handed operable needle module connection system with an upper and lower end connected.

The DC Motor 15 (FIG. 1) provides rotational movement to the lower end disposable needle module 200 (FIG. 2). The upper end 100 of FIG. 1 is completely sealed from the lower end disposable needle module 200.

FIGS. 2A, 2B, 3A, 3B illustrate a preferred embodiment of the present invention of the lower end disposable needle module 200. Corresponding Part Numbers are as follows:

| ITEM NO. | DESCRIPTION |
| --- | --- |
| 1 | Housing, Right |
| 2 | Yoke |
| 3 | Coupling |
| 4 | Roller |
| 5 | M1X4 DOWEL PIN W/ SPHERICAL ENDS |
| 6 | Bell Crank |
| 7 | Connecting Rod |
| 8 | Housing, Left |
| 9 | Lock Spring |
| 10 | Slider |
| 11 | Bayonet Cup |
| 12 | Detent |
| 13 | Needle Cup |
| 14 | Needle Core |
| 15 | Needle |
| 16 | Depth Cup |
| 17 | Bellows |
| 18 | Silicone Fluid |
| 19 | Dowel Pin, 5 mm long × 2 mm dia |
| 20 | Dowel Pin, 8 mm long × 1.5 mm dia |
| 21 | UV Cure Glue |

Figure 4A:
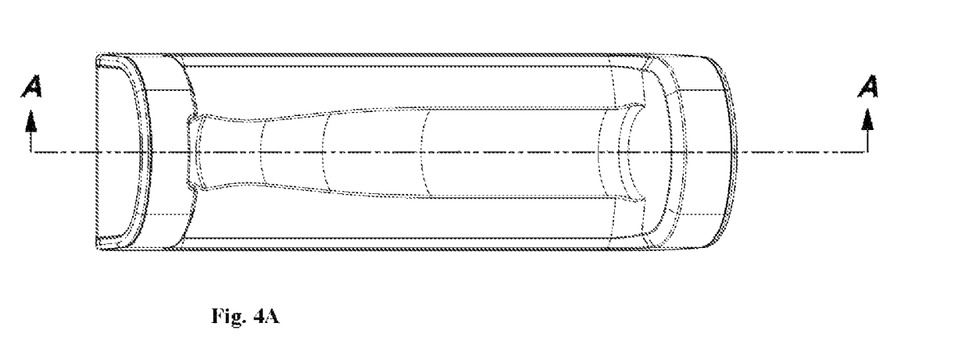
FIG. 4A shows a preferred embodiment of a battery recharging cradle.
Figure 4B:
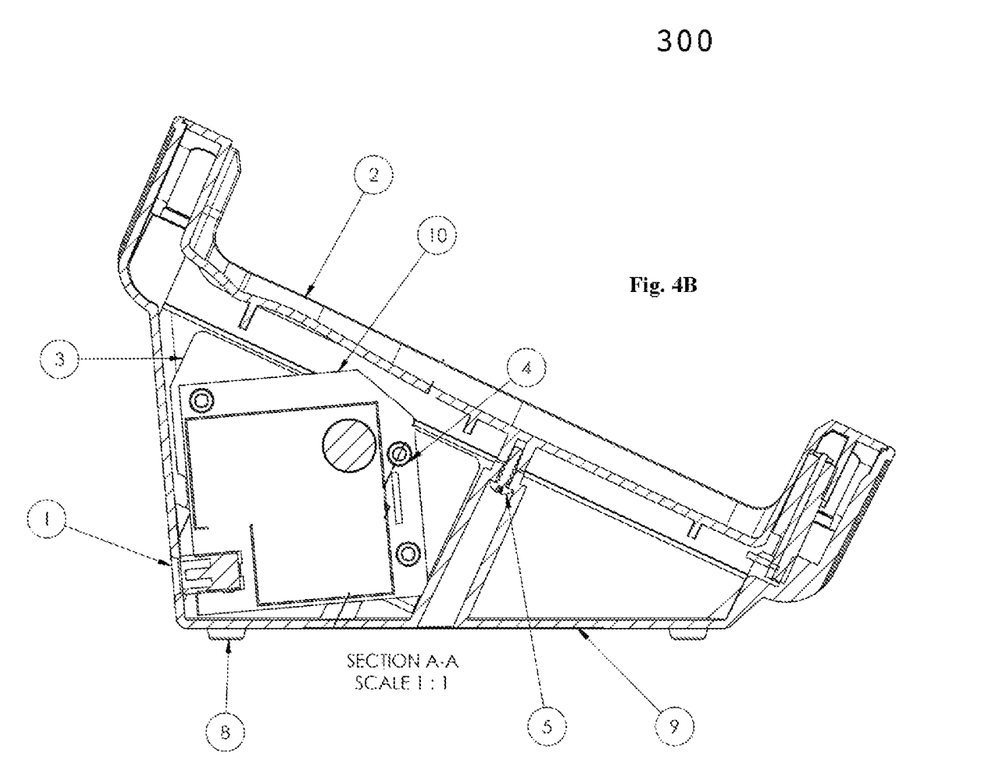
FIG. 4B shows a cut away of the preferred embodiment of a battery recharging cradle.

The general mechanism for moving the needles 15 employs a yoke 2 and a bell crank 6 with slotted ends to drive a connecting rod 7. The needles 15 are embedded in needle cup 13. A bellow 17 keeps the disposable lower end needle module 200 sealed away from action of the connecting rod 7. The action of the connecting rod 7 is coupled to needle cup 13 that reciprocates up and down so needles 15 can penetrate the skin. Detents 12 in the depth cup 16 allow a user to feel a click in resistance and adjust the depth that the needles 15 will move from 0.0 to 2.5 mm. To engage the disposable lower end needle module 200 to the pen upper end 100 they are pushed axially together and then twisted to lock in place. Referring to FIGS. 4A, 4B a recharging cradle 300 is disclosed to safely hold and charge the pen upper end 100 battery 16 (FIG. 1) comprising the following:

| ITEM NO. | DESCRIPTION |
| --- | --- |
| 1 | Charger, Bottom |
| 2 | Charger, Top |
| 3 | Bracket |
| 4 | SHCS 6-32 |
| 5 | THREAD FORMING SCREW, 4-20 |
| 6 | THREAD FORMING SCREW, 4-20 |
| 7 | Spacer |
| 8 | Bumper |
| 9 | Label |
| 10 | PCBA Cable Subasm |

The battery 16 (FIG. 1) is sealed inside the upper end 100. When the upper end 100 is placed on to the recharging cradle 300 charger top 2 (FIG. 4, 4A) the PCBA Assem 18 (FIG. 1) is in close proximity to PCBA cable subasm 10 (FIG. 4, 4A) so that when current is applied the battery 16 can be charged through inductive charging. This is a safety feature because neither the recharging cradle 300 nor the upper end 200 are opened up and plugged in to each other. The upper end 100 and recharging cradle 300 can be easily cleaned with ethanol wipes between charging or sterilized by other chemical treatment. The cradle is designed to safely hold the pen upper end 100 during charging and storage.

According to one aspect of an exemplary embodiment of the present invention, depicting a collagen stimulating device which utilizes a single handed operable needle module connection system, including needle(s) 15 which insert into the dermis layer of the skin to allow for stimulation of collagen growth. The collagen stimulating device, in the form of a reciprocating shaft device, consists of an upper end 100 and a lower end disposable needle module 200. The upper end 100 is a durable assembly; while the lower end disposable needle module 200 is disposable. Inside the lower end disposable needle module 200 is a needle cup 13. When the needle cup 13 is extended, the needle(s) 15 will protrude from the lower end disposable needle module 200 by the reciprocating connecting rod 7. The lower end disposable needle module 200, will allow for increased safety, through a lowered chance of cross-contamination and single use application.

The lower end disposable needle module 200 is where the reciprocating connecting rod 7 is applied to a workpiece, as for example, when used, a needle is applied to the skin of the recipient (not shown). The upper end 100 is the opposite end from the lower end disposable needle module 200 reciprocating connecting rod 7. When the lower end disposable needle module 200 reciprocating connecting rod 7 is held against the workpiece, such as human skin, the needle(s) 15 will penetrate the epidermis and to the epidermis, causing the stimulation of collagen.

Concentrically within the reciprocating shaft device is a shaft assembly which has a circular cross section. The shaft assembly has two sections, namely an upper section, and a lower section. The upper section is located toward the upper end of the reciprocating shaft device and the lower section is located toward the lower end of the reciprocating shaft device. The lower section of the shaft assembly contains needles which when the shaft assembly is released may pierce the epidermal layer of human skin, thereby stimulating the release of collagen. The needle(s) 15 may be injected into the skin, by way of numerous embodiments, which shall be detailed, hereinafter.

A coil assembly is mounted symmetrically about the shaft assembly toward the upper end of the reciprocating shaft device. The coil assembly includes a spring located within an inner housing. The coil encases nearly all of the upper section of the shaft assembly and a small part of the lower section of the shaft assembly adjacent to the upper section. The needle(s) 15 on the shaft assembly may either be in rows, or concentric circles or overlapping to create uniform stimulation of the skin.

1. Conversion of Rotation into Reciprocation

Referring to FIGS. 1-3B, the lower end disposable needle module 200 converts the rotary motion from the upper end 100 into reciprocating motion for the movement of needles 15 that create micro-channels in the skin. This mechanical injury of the skin prompts the skin to heal itself and generate collagen, etc. This mechanism employs a scotch yoke 2 and a bell crank 6 with slotted ends to drive a connecting rod 7. The motion is 2.75 mm total translation per cycle. This allows a needle cup 13 to create 1400 holes per second at a speed of 7000 rpm. The motor 15 (FIG. 1) is capable of oscillating needle(s) 15 (FIG. 2A,2B,3A,3B) at between 1000-10,000 rpm. More needle(s) 15 and/or increased speed will permit the generation of more micro-channels per second. Other forms of translating rotation into reciprocation may be used. This novel feature makes the pen more reliable and also prevents other disposables from interacting with the upper end. The coupling 3 rotates and drives the eccentric roller 4. This action causes the yoke 2 to oscillate back and forth in a linear motion. The bell crank 6 multiplies this motion and redirects motion to oscillate the connecting rod 7, which is coupled to the needle cup 13, needle core 14 and needle(s) 15. So the needle(s) reciprocate in and out of the skin and may penetrate the patient's skin when the depth cup 16 is adjusted to expose the needles 15. Dowel pins 5, 19, 20 facilitate the conversion of rotary motion to linear reciprocation motion. The high speed movement of the yoke 2 and roller 4 against the housing left 8 and housing right 1 is facilitated by the presence of lubricant silicone fluid 18.

2. Single Use of Disposable and Needle Retraction During Power Shutdown

In order for the user to attach the lower end disposable needle module 200 to the upper end, they must line up a d-shaped disposable coupling of the lower end disposable needle module 200 with a corresponding d-shaped shaft on the upper end 100. The user must align the d-shaped shaft of the upper end 100 with the d-shaped opening of the coupling 3 (FIG. 2A, 2B, 3A, 3B). Then push the lower end disposable needle module 200 onto the upper end 100 and rotate the bayonet cup 11 to engage the male lugs of the upper end 100. This action pushes the slider 10 (FIG. 2A, 2B, 3A, 3B) forward and lets the lock spring 9 drop onto the pen shaft. Further rotation by the user fully engages the bayonet cup 11 onto the upper end 100. There is only one way to attach the lower end disposable needle module 200 to the upper end 100 to ensure the rotational orientation of the lower end disposable needle module 200 and upper end 100 for keying the low point of the reciprocation motion. By sliding the upper end pen tip 1 (FIG. 1) into lower end disposable needle module 200 (FIGS. 2A, 2B, 3A, 3B), the home position of the lower end disposable needle module 200 reciprocation low point is known and the pen software will turn the lower end disposable needle module 200 end so the low point of reciprocation is located during power shutdown. This brings the needle(s) 15 inside the depth of the depth cup 16 by at least 0.25 mm at all times (more if the depth cup 16 is set to a lower depth). Also, this arrangement ensures the needle(s) 15 can only be set to penetrate the skin by a maximum of 2.5 mm. Furthermore, when the pen tip 1 (FIG. 1) is inserted into the bayonet cup 11 is pushed along a locking spring 9 and into the lower end disposable needle module 200. This action loads the locking spring 9 and upon removal of the lower end disposable needle module 200, the locking spring 9 is free to bend upwards and block the re-insertion of the lower end disposable needle module 200. This makes the lower end disposable needle module 200 a single use device.

3. Adjustment of Micro-Channel Depth on Disposable

The depth adjustment for the needle(s) 15 is located on the lower end disposable needle module 200—not on the upper end 100. This means the depth cup 16 can be turned from its initial position of 0 depth through 11 distinct depth settings, each 0.25 mm deeper, until it reaches a limit of 2.5 mm. The detent 12 gives sensory feedback to the user and effectively locks the position, detent 12 also interferes with the depth cup 16 at the 0 mm depth to prevent any further depth inward setting less than 0.0 mm. For the 2.5 mm depth the depth cup 16 back element prevents adjusting the depth greater than 2.5 mm. The depth cup 16 has markings and numbers to identify the depth setting. Adjustment of the depth on the lower end disposable needle module 200 instead of the upper end 100 means only one hand of the user is contaminated. The other hand is on a protective sheath over the upper end 100.

Depth Setting

The user may twist the depth cup 16 relative to the bayonet cup 11 to reveal more of the needle(s) 15 length. This depth adjustment is facilitated by three items. First the depth cup 16 may not be adjusted below zero (0) where the depth cup 16 is trapped by the retention feature on the housing left 8. Also the depth cup 16 may not go above the highest setting of 2.5 where the depth cup 16 stops turning against the bayonet cup 11. For other settings the depth cup 16 has slots that engage the flexible detent 12 to enable intermediate depth settings. The thread pitch of the depth cup 16 is such that axial force on the tip is not great enough to cause rotation of the depth cup 16 and alter the setting.

4. Prevention of Fluid from Entering the Pen During Treatment

The blockage and elimination of fluids from the patient entering the upper end 100 is addressed by multiple features. First the lower end disposable needle module 200 has a tight fitting bellows 17 that is sealed around connecting rod 7. Second, the inner cup back (16) is effectively sealed against the pen bayonet lock. Third, the pen has an integral rotary seal (15) that serves as an extra barrier during treatment, but the primary barrier when the disposable lower end is removed and the pen is still present in the treatment arena. The inner cup back element (16) has a raised feature to capture the protective sheath and the protective sheath keeps the pen contaminant free during use.

Typical Use

The bellows 17 prevent migration of gels used during treatment to the mechanism and also prevents migration of blood to the pen. The presence of glue 21 aids in securing the needles 15 to the needle core 14 to avoid any needles being retained in the patient's skin during treatment.

Alternative embodiments may include differing needle shapes, such as a star or x-shape reduce the cross-section of the needle point over a certain depth of penetration into the dermis. A further alternative embodiment may include a drug delivery system, in the form of an internal reservoir or an attached cartridge, along with a hypodermic needle from which to inject a drug or skin formulation. In yet another alternative embodiment, the device contains a depth sensor and alarm to notify a user when the needle(s) have reached the appropriate depth. In yet another alternative embodiment, the device contains an actuator to control the speed, depth and dwell time of needle penetration. In yet another alternative embodiment, the device will contain a processor and communication module, such as a Wi-Fi, radio, or blue tooth transmitter, allowing one- or two-way transmission of data to a software application for data analysis, and prescription purposes; dosage, time, depth depending on the medication, tracking.

While preferred embodiments of the invention have been illustrated, it will be obvious to those skilled in the art that various modifications and changes may be made thereto without departing from the spirit and scope of the invention as hereinafter defined in the appended claims.

We claim:

1. A device for stimulating collagen growth in a human, the device comprising:
   an upper end including a motor;
   a lower end disposable needle module comprising a lock spring and a connecting rod, the connecting rod attachable to at least one needle and when the lower end disposable needle module is detached from the upper end, the lock spring moves to a position wherein the lower end disposable needle module cannot be re-attached to the upper end; and
   a coupling attached to an eccentric roller; the eccentric roller coupled to a yolk, the yolk coupled to a bell crank, and the bell crank attachable to the connecting rod, wherein the motor turns the coupling and the eccentric roller, the eccentric roller engages the yolk to oscillate and the yolk oscillates the bell crank and the bell crank moves the connecting rod and the at least one needle.

2. The device of claim 1 wherein the at least one needle reciprocates at between 1,000-10,000 rpm.

3. The device of claim 1 wherein the at least one needle includes an adjustment for depth of penetration from 0-2.5 mm.

4. The device of dam 1 wherein the at least one needle includes an adjustment for depth of penetration in 0.25 mm increments.

5. The device of claim 1 wherein the attachment comprises the steps of inserting the upper end tip into the lower end disposable needle module and twisting the upper end relative to the lower end disposable needle module to a locked position.

6. The device of claim 1 wherein the connecting rod is sealed with a bellows.

7. The device of claim 1 further comprising a power source positioned within the upper end.

8. The device of claim 7 wherein the power source is rechargeable.

9. The device of claim 1 wherein the motor provides rotary motion that is converted to reciprocating motion by the eccentric roller, the yolk, and the bell crank.

10. The device of claim 9 wherein the reciprocating motion includes a high point wherein the at least one needle is exposed beyond a tip end of the lower end disposable needle module and a low point wherein the at least one needle is retracted within the tip end of the lower end disposable needle module.

11. The device of claim 10 wherein attachment of the upper end to the lower end disposable needle module initiates software in the device to position the at least one needle at the low point.

12. The device of claim 10 wherein during power shutdown of the device, software in the device returns the at least one needle to the low point.

13. The device of claim 1 wherein the at least one needle is arranged in concentric circles.

14. The device of claims 1 and 2-6, wherein the needle is X-shaped.

15. A method for stimulating collagen growth, the method comprising: operating the device of claim 1 using one hand and without contamination when the at least one needle penetrates skin.

* * * * *